United States Patent
Tayebi

(10) Patent No.: US 9,173,770 B1
(45) Date of Patent: Nov. 3, 2015

(54) PUNCTAL PLUGS FOR INSERTION INTO THE TEAR DUCTS TO SLOW DRAINAGE OF EYE MOISTURE AND METHODS FOR THE MANUFACTURE THEREOF

(71) Applicant: Amad Tayebi, Westford, MA (US)

(72) Inventor: Amad Tayebi, Westford, MA (US)

( * ) Notice: Subject to any disclaimer, the term of this patent is extended or adjusted under 35 U.S.C. 154(b) by 349 days.

(21) Appl. No.: 13/694,616

(22) Filed: Dec. 17, 2012

Related U.S. Application Data

(63) Continuation-in-part of application No. 12/156,890, filed on Jun. 5, 2008, now Pat. No. 8,334,008.

(60) Provisional application No. 60/933,200, filed on Jun. 5, 2007.

(51) Int. Cl.
*A61L 33/06* (2006.01)
*A61F 9/00* (2006.01)
*B29C 47/02* (2006.01)

(52) U.S. Cl.
CPC ............... *A61F 9/00* (2013.01); *B29C 47/025* (2013.01)

(58) Field of Classification Search
None
See application file for complete search history.

(56) References Cited

U.S. PATENT DOCUMENTS

2007/0233037 A1* 10/2007 Gifford et al. ............... 604/521

* cited by examiner

*Primary Examiner* — John J Figueroa
(74) *Attorney, Agent, or Firm* — Amad Tayebi; American Patent Associates

(57) ABSTRACT

A method is disclosed for making a porous punctal plug by providing a multi-filament fibrous strand and extrusion coating the fibrous strand with a polymeric material coating and cutting the coated fibrous strand to adequate length for insertion into a mammal's punctal opening.

10 Claims, 7 Drawing Sheets

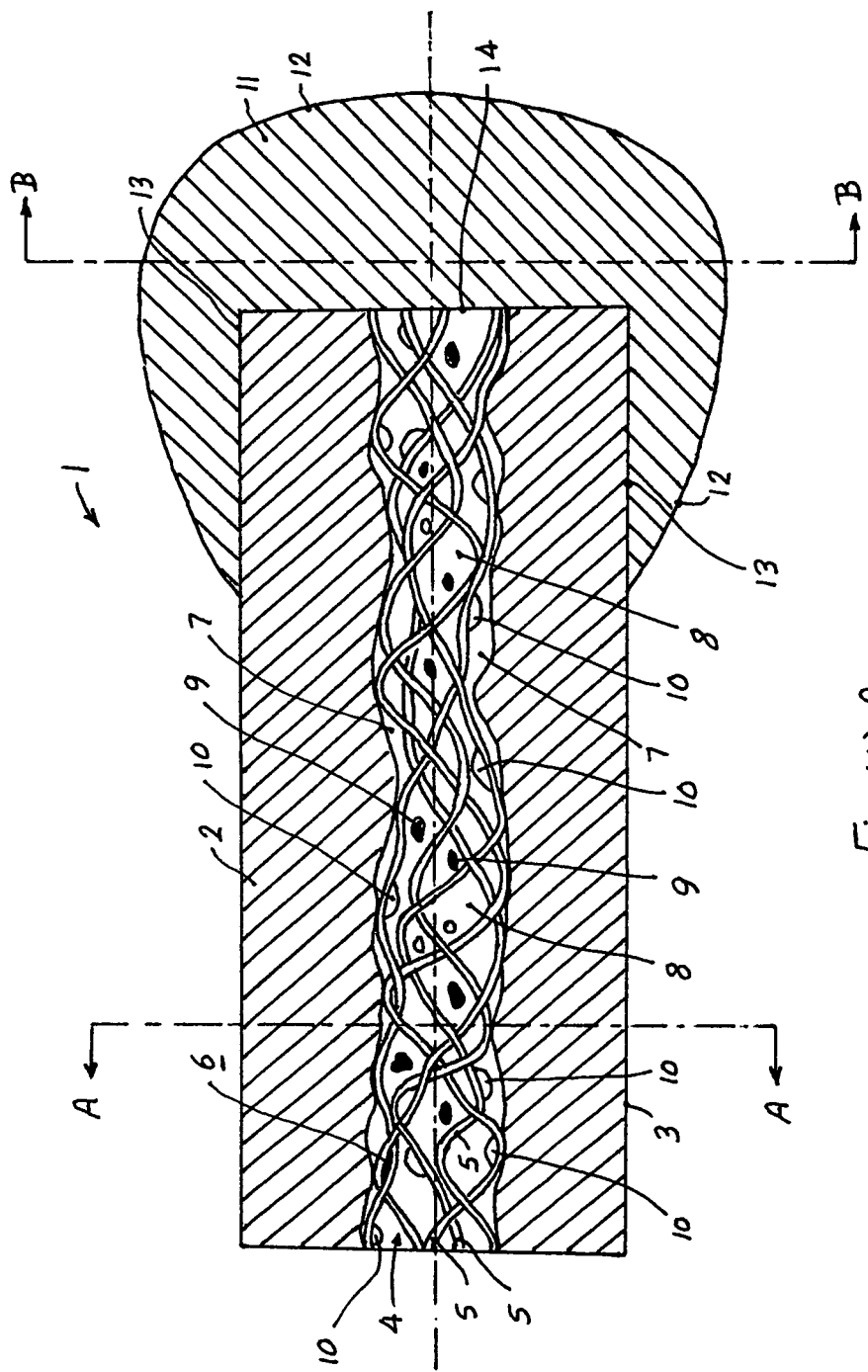
Fig. (1) A

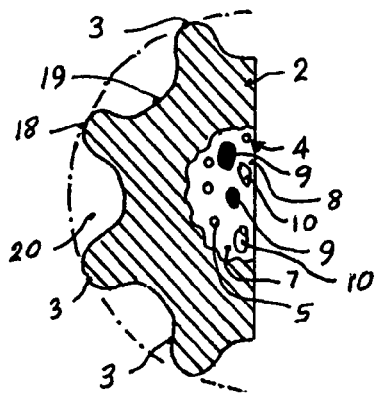
Fig.(1)B
(Section A-A)1
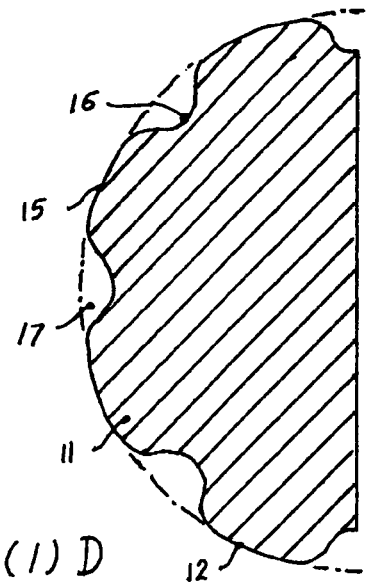
Fig.(1)D
(Section B-B)1
Fig.(1)E
Section B-B)2
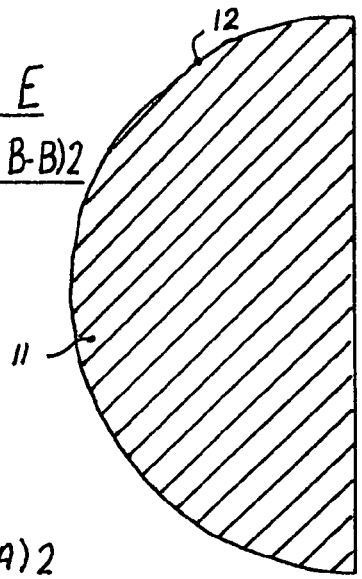
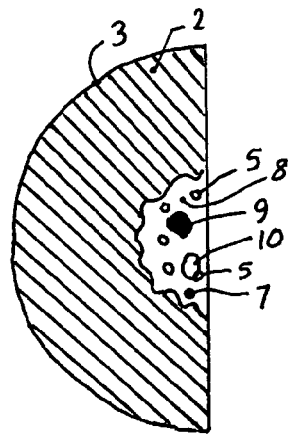
Fig.(1)C
(Section A-A)2

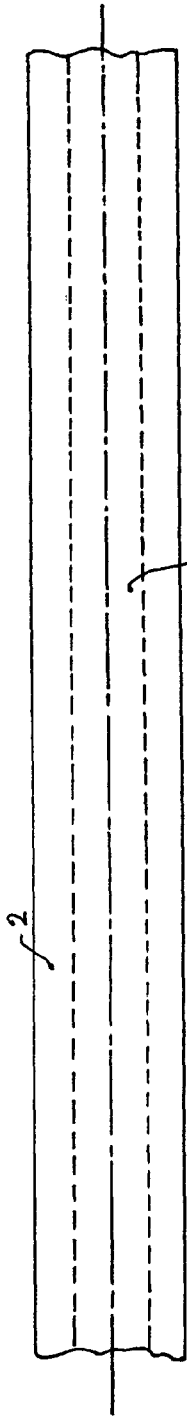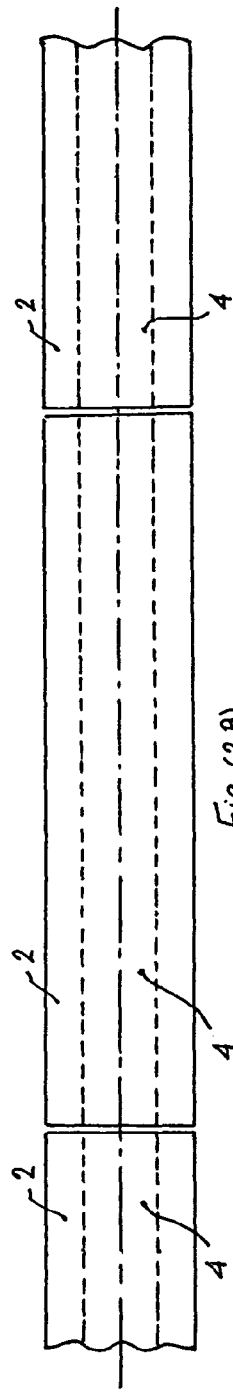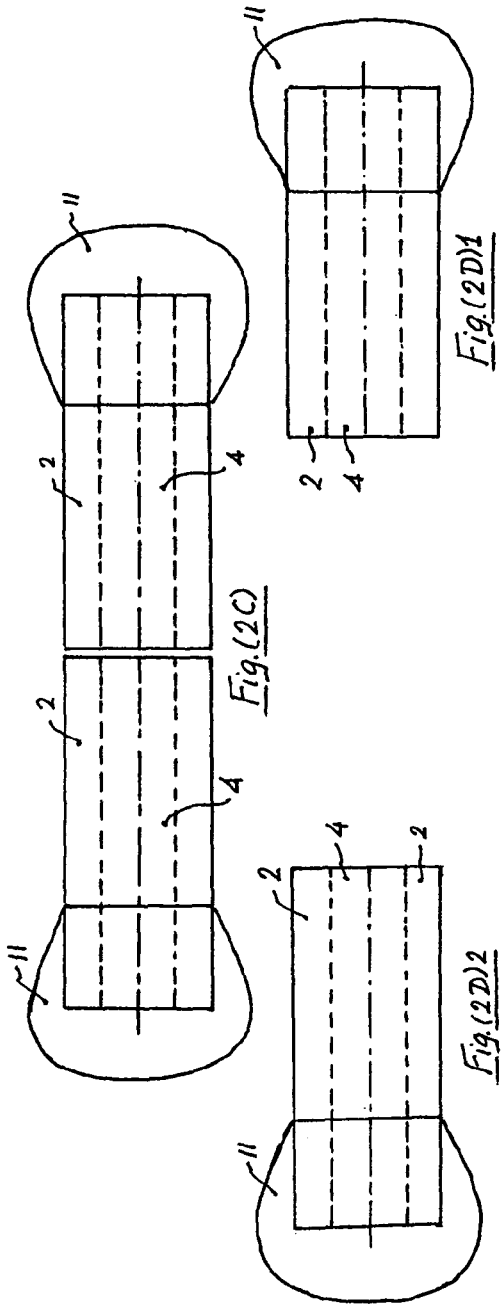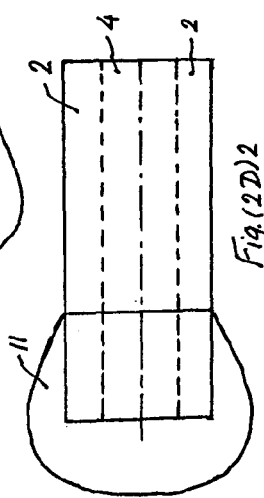

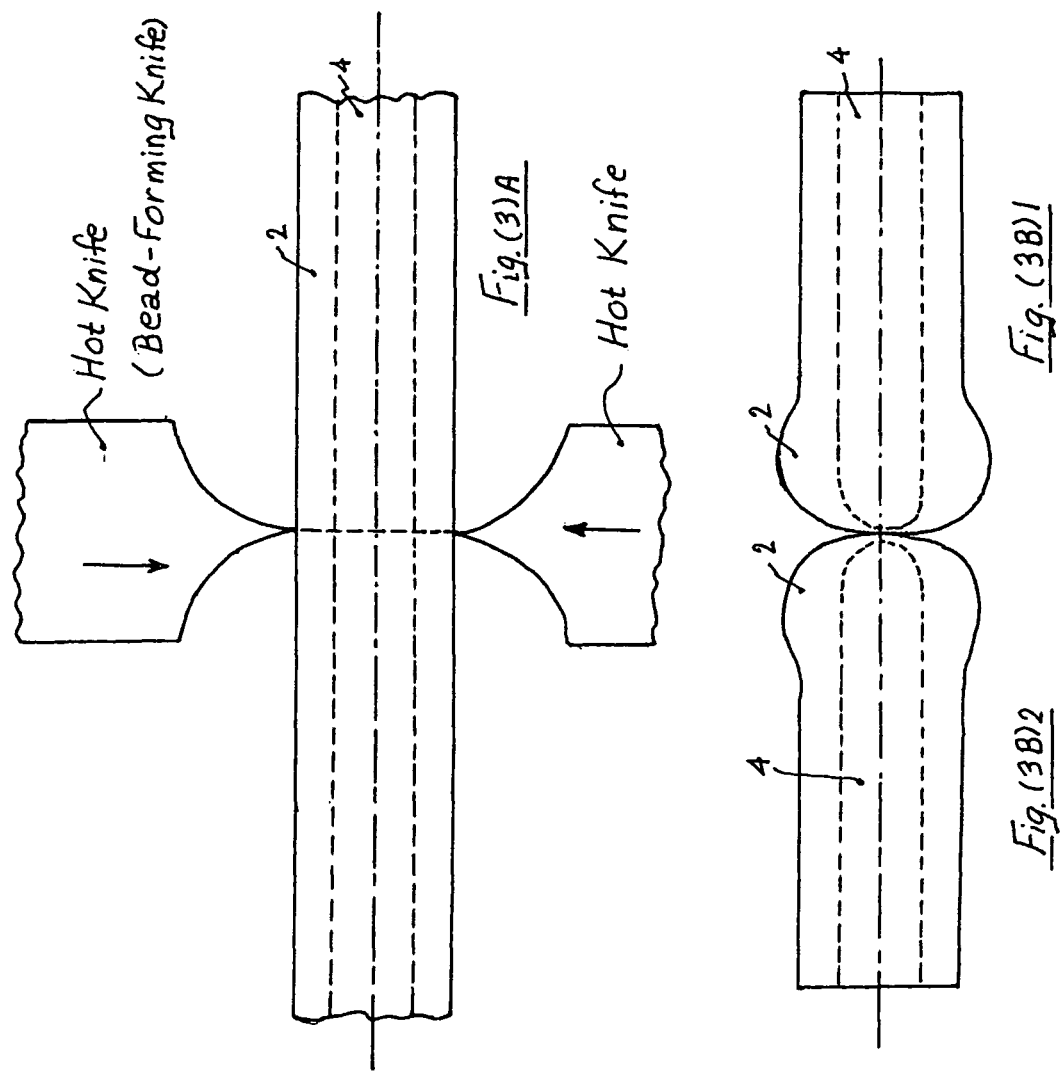

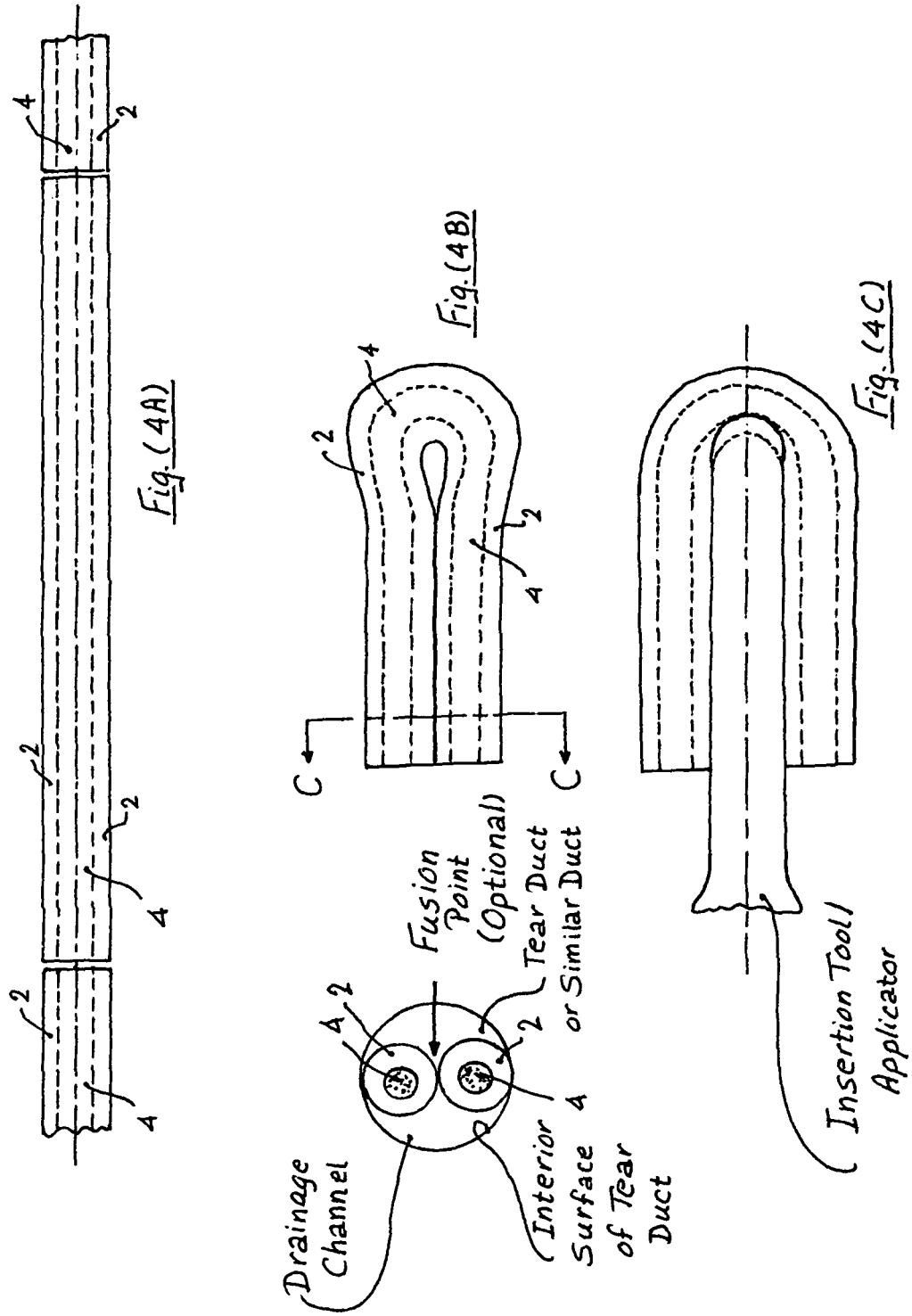

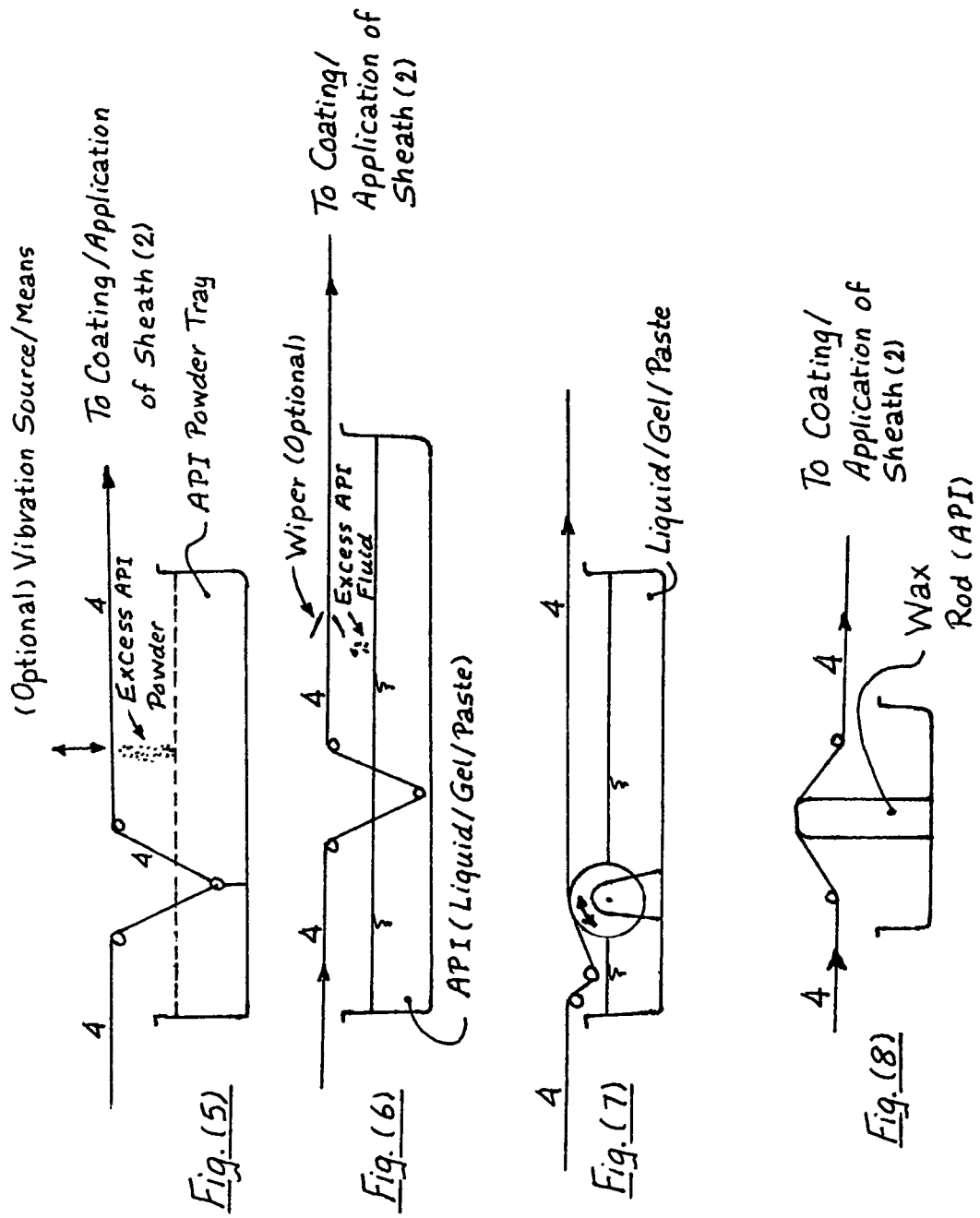

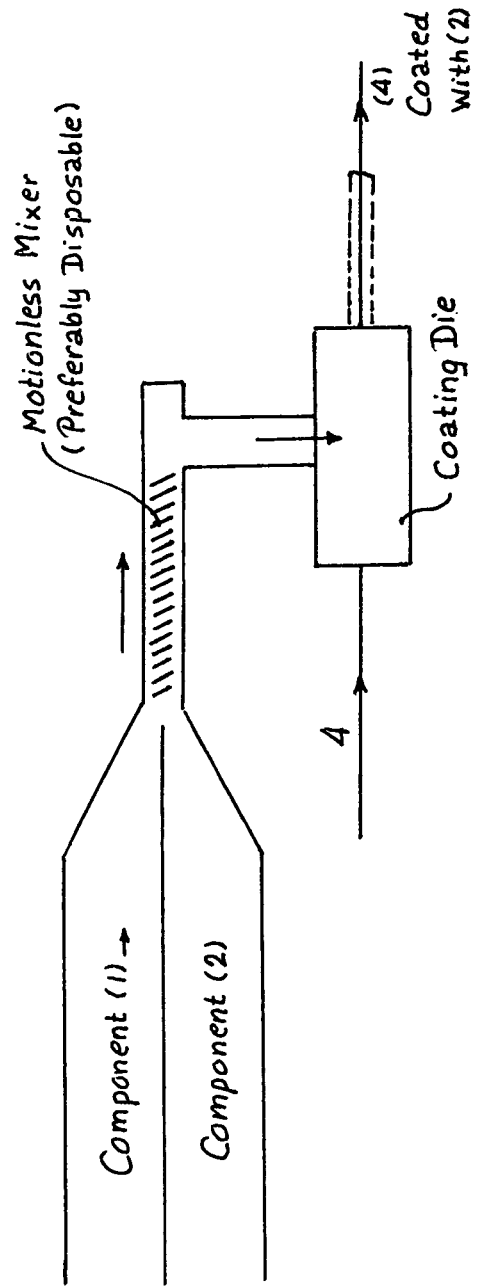
Fig. (9)

PUNCTAL PLUGS FOR INSERTION INTO THE TEAR DUCTS TO SLOW DRAINAGE OF EYE MOISTURE AND METHODS FOR THE MANUFACTURE THEREOF

STATEMENT REGARDING RELATED PATENT APPLICATIONS

This Continuation in Part (CIP) utility patent application claims priority from utility patent application Ser. No. 12/156,890 (filing date Jun. 5, 2008) which is scheduled to issue on Dec. 18, 2012 as U.S. Pat. No. 8,334,008. Application Ser. No. 12/156,890 claims priority from Provisional Patent Application, Ser. No. 60/933,200 filed on Jun. 5, 2007. As such, this application also claims priority of Ser. No. 60/933,200 and incorporates by reference and in their respective entireties each of application Ser. No. 12/156,890 and 60/933,200.

FIELD OF THE INVENTION AND AN OVERVIEW OF THE INVENTION

The present invention is in the field of manufacturing small diameter porous punctal plugs. More particularly, it relates to porous fibrous material punctal plugs to be used to slow down the rate of drainage of eye fluids (tear liquid) through the canalicular canal of the eye for the treatment of dry eye condition.

Upon insertion in the punctal opening(s), the porous fibrous material punctal plug of the present invention provides an increased surface area (the exterior surface area of the fibers) and thus an increased resistance to flow of the eye fluid through the punctal openings and through the upper and lower canaliculus to the lacrimal sac. At its narrowest segment, the canaliculus measures about 0.5 millimeter in diameter and, thus, presents a challenge for manufacturing very small diameter porous punctal plugs. The present invention makes it possible to produce very small diameter porous punctal plugs by extrusion coating a porous fibrous strand with a thin layer of polymeric material coating. The number of fibers comprising the fibrous strand and their denier and texture and the density of the fibrous strand control the resistance to flow through the porous punctal plug and thus the rate of drainage of the tear liquid. The present invention also provides a low cost tooling and processing method of making such porous punctal plugs and porous punctal plugs made accordingly. In comparison to the prior art methods of injection molding punctal plugs and injection over-molding onto fibrous material-type porous masses, the present invention makes it possible to produce extremely small diameter punctal plugs, as low as 0.25 millimeter in diameter.

BACKGROUND OF THE INVENTION AND RELATED PRIOR ART

Examination of the prior art reveals a large number of patents and pending patent applications that relate to the subject matter of the present invention, for example, U.S. Pat. Nos. 3,949,750, 5,171,270, 5,283,063, 5,437,625, 5,469,867, 5,593,393, 5,723,005, 5,817,335, 5,962,548, 6,020,445, 6,099,852, 6,234,175, 6,238,363, 6,306,114, 6,367,929, 6,428,502, 6,679,605, 6,822,016, 6,923,800, 7,998,497, 8,277,830 and 8,298,578 and U.S. Pending Application No. US 20050095269, 20050197614, 20050232972, 20060106352, 20060172972, 20070233037, 20070298075, 20070299516, 20080045911, 20080114076 and 20090240276. Each of these listed Patents and Pending Patent Applications and their respective teachings are incorporated in the present invention, in their respective entireties, by reference.

DESCRIPTION OF THE INVENTION

Referring to FIGS. 1 to 9, the numbers used in the drawings to identify elements, components or locations shown in the drawings are described as follows:

1: Porous punctal plug. Also, alternatively, referred to as article for dispensing medicinal ingredients
2: Exterior sheath of 1 or body of extrusion-coated porous punctal plug. Exterior sheath 2 is made of a polymeric material which may be a thermoplastic or thermoset material.
3: Exterior surface of 2
4: Fibrous Core (multi-filament strand) contained within 2. Strand 4 may be in the form of a multi-filament yarn or tow made of continuous or discontinuous (staple) fibers and/or filaments. Strand may be twisted or untwisted. Strand may be needled or un-needled. Fibers/Filaments of the strand may be bio-absorbable or may comprise bio-absorbable fibers, segments or portions. Strand may be in the form of a braid (circular or flat). The braid may have core element(s) or may have no core element. Fibers comprising the strand may be untextured (flat) or textured and/or have straight segments and/or crimped textured segments. Fibers comprising the strand have inter-fiber spacings (8) and high capillary action inter-fiber contact points (6). Core elements of braid-type strand may be straight fibers and/or crimped fibers. Alternatively, fibrous core 4 may be in the form of a monofilament impregnated with an A.P.I. (Active Pharmaceutical Ingredient). Multi-filament strand may also be made of cohesively bonded fibers. Cohesively bonded fibers are defined as fibers bonded together by a melting action at the fiber surfaces at cross-over points of the fibers and co-solidification upon cooling.
5: Fibers comprising fibrous core/multi-filament strand 4.
6: High capillary action inter-fiber contact points.
7: Spacings between interior surface of exterior sheath 2 and fibers of fibrous core/multi-filament strand 4.
8: Inter-fiber spacings.
9: Medicinal ingredient (Active Pharmaceutical Ingredient API) in powder/particulate form.
10: Active Pharmaceutical Ingredient, (API) in liquid, wax, gel or paste form.
11: End sealing bead.
12: Exterior surface of end sealing bead 11.
13: Bonding surface between end sealing bead 11 and exterior surface 3 of exterior sheath or body of punctal plug 2.
14: Interior surface of end sealing bead 11 facing cross-section of fibrous core 4.
15: Peaks of exterior surface 12 of end sealing bead 11 for the case when end sealing bead 11 is, optionally, embossed.
16: Valleys of exterior surface 12 of end sealing bead 11 for the case when end sealing bead 11 is, optionally, embossed.
17: Drainage channels formed/created between the interior surface of tear duct(s) and the exterior surface 12 of end sealing bead 11.
18: Peaks of exterior surface (3) of exterior sheath or body of punctal plug 2 of article 1, for the case when the exterior sheath or body of punctal plug 2 is, optionally, having a corrugated surface.
19: Valleys of exterior surface (3) of exterior sheath or body of punctal plug 2 of article 1, for the case when the exterior sheath or body of punctal plug 2 is, optionally, having a corrugated surface.

20: Drainage channels formed/created between the interior surface of tear ducts and exterior surface (3) of exterior sheath or body of punctal plug 2 of article 1.

BRIEF DESCRIPTION OF THE DRAWINGS

FIG. (1)A is a Front Longitudinal-Sectional View of Article 1.

FIG. (1)B shows one half of (Section A-A) of Article 1.

FIG. (1)C shows one half of another alternative of (Section A-A) of Article 1.

FIG. (1)D shows one half of (Section B-B) of Article 1.

FIG. (1)E shows one half of another alternative of (Section B-B) of Article 1.

FIG. (2A) shows a longitudinal view of exterior sheath 2 of article 1 or body of porous punctal plug and fibrous core 4.

FIG. (2B) shows a longitudinal view of exterior sheath 2 of article 1 or body of porous punctal plug and fibrous core 4 cut into separate segments.

FIGS. (2C), (2D)1 and (2D)2 show longitudinal views of assemblies comprising exterior sheath 2 of article 1 or body of porous punctal plug, fibrous core 4 and end sealing bead 11.

FIG. (3)A shows a longitudinal view of exterior sheath 2 of article 1 or body of porous punctal plug and fibrous core 4 and hot bead-forming knives prior to cutting exterior sheath 2 and fibrous core 4.

FIGS. (3B)1 and (3B)2 show a longitudinal view of exterior sheath 2 of article 1 or body of porous punctal plug and fibrous core 4 after being cut by hot bead-forming knives.

FIG. (4A) shows a longitudinal view of exterior sheath 2 of article 1 or body of porous punctal plug and fibrous core 4 cut into separate segments prior to being folded as shown in FIG. (4B).

FIG. (4B) shows a longitudinal view of a segment of exterior sheath 2 of article 1 or body of punctal plug and fibrous core 4 after being folded, as shown, and a cross-sectional view C-C showing folded segment surrounded by tear duct or similar duct and drainage channel.

FIG. (4)C shows insertion tool/applicator.

FIG. 5 shows fibrous core 4 being guided through an API (Active Pharmaceutical Ingredient) powder tray then being directed to coating/application of sheath 2.

FIG. 6 shows fibrous core 4 being guided through an API (Active Pharmaceutical Ingredient) liquid/gel/paste then being directed to coating/application of sheath 2.

FIG. 7 shows fibrous core 4 being guided over a roll placed in a liquid/gel/paste tray.

FIG. 8 shows fibrous core 4 being guided over an API wax rod then being directed to coating/application of sheath 2.

FIG. 9 shows two components (component (1) and component (2)) directed into a motionless mixer then into a coating die in which fibrous core 4 is fed in and exits coated with sheath 2. Alternatively, coating die may be fed molten thermoplastic polymeric material from a plasticating extruder

DETAILED DESCRIPTION OF THE INVENTION

With reference to FIGS. 1 to 9, and the numbers used in the drawings to identify elements, components or locations shown in the drawings, the present invention discloses a method of making a porous punctal plug. The method comprises the steps of providing a multi-filament strand, extrusion-coating the exterior surface of said strand with a polymeric material, and cutting the coated strand to desired length which is suitable for insertion into a mammal's punctal opening.

The active pharmaceutical ingredient (API) may be in a powder/particulate form, in the form of a gel, a liquid or a paste or in the form of a wax, Also, coating the exterior surface of fibrous core 4 with an impermeable coating/exterior sheath 2 is at a temperature not exceeding the maximum temperature the active pharmaceutical ingredient (API) may sustain without adversely impacting its (the API's) medicinal and performance properties. Exterior sheath 2 is a soft (low modulus) biocompatible material. For example, Elvax R ethylene vinyl acetate (EVA) resin made by DuPont, Elvax 3175 LG, having a melting point of 69 C (156 F) or similar and biocompatible material.

The coating process may be accomplished i) by a thermoplastic polymeric material extrusion through a wire coating type die, or ii) by application of a self-curing single or multiple component resin, for example, Room Temperature Curing Liquid Silicone Rubber (LSR).

For maintaining a uniform coating around fibrous core 4 and ingredient 9 and/or 10, application of tension on fibrous core 4 and alignment of axis of fibrous core 4 to be along the axis of coating die are essential process control parameters.

The above described method may also include the steps of a) sealing at least one end of cut length of coated strand by i) application of a bead 11 at said at least one end (see FIG. 2) and, optionally, embossing bead 11, (see FIG. 1)D, or ii) by hot sealing cut points by using specially profiled heated knives (see FIG. 3) or b) folding cut length into a hair-pin form suitable for insertion into tear ducts or similar ducts (see FIG. 4).

The invention claimed is:

1. A method of making a porous punctal plug for insertion into the punctal openings of the eyes of a mammal for reducing the drainage rate of eye fluids, said method comprising the steps of:
   providing a multi-filament strand,
   extrusion coating the exterior surface of said multi-filament strand with a polymeric material,
   and
   cutting the coated multi-filament strand to a desired length suitable for insertion into a punctal opening of said mammal's eye.

2. The method of making a porous punctal plug in accordance with claim 1 wherein said multi-filament strand being in the form of a continuous multifilament yarn.

3. The method of making a porous punctal plug in accordance with claim 1 wherein said multi-filament strand being in the form of a discontinuous (staple) multi-filament yarn.

4. The method of making a porous punctal plug in accordance with claim 1 wherein said multi-filament strand being in the form of a textured multifilament yarn.

5. The method of making a porous punctal plug in accordance with claim 1 wherein said multi-filament strand being in the form of a braid.

6. The method of making a porous punctal plug in accordance with claim 1 wherein said multi-filament strand being in the form of a cohesively-bonded multi-filament yarn.

7. The method of making a porous punctal plug in accordance with claim 1 wherein said polymeric material being a thermoplastic material.

8. The method of making a punctal plug in accordance with claim 1 wherein said polymeric material being a thermoset material.

9. The method of making a porous punctal plug in accordance with claim 1 wherein said polymeric material being a silicone material.

10. A porous punctal plug made in accordance with claim 1.

* * * * *